United States Patent
Leuckel

(10) Patent No.: US 11,432,957 B2
(45) Date of Patent: Sep. 6, 2022

(54) MALE URINARY FLOW DIRECTING DEVICE

(71) Applicant: Harrison Bert Leuckel, Allentown, PA (US)

(72) Inventor: Harrison Bert Leuckel, Allentown, PA (US)

(*) Notice: Subject to any disclaimer, the term of this patent is extended or adjusted under 35 U.S.C. 154(b) by 393 days.

(21) Appl. No.: 16/533,724

(22) Filed: Aug. 6, 2019

(65) Prior Publication Data
US 2020/0129322 A1 Apr. 30, 2020

Related U.S. Application Data

(60) Provisional application No. 62/751,372, filed on Oct. 26, 2018.

(51) Int. Cl.
| | | |
|---|---|---|
| A61F 5/453 | (2006.01) | |
| A61F 13/471 | (2006.01) | |
| A61F 5/44 | (2006.01) | |

(52) U.S. Cl.
CPC ............ *A61F 5/453* (2013.01); *A61F 13/471* (2013.01); *A61F 2005/4402* (2013.01)

(58) Field of Classification Search
CPC . A61F 5/453; A61F 13/471; A61F 2005/4402
USPC ........................................................ 604/349
See application file for complete search history.

(56) References Cited

U.S. PATENT DOCUMENTS

| | | | | |
|---|---|---|---|---|
| 2,878,486 A | * | 3/1959 | Bartlett ................. | A61F 5/4556 4/144.4 |
| 4,590,931 A | * | 5/1986 | Kidwell, Jr. .............. | A61F 5/40 128/DIG. 15 |
| 4,790,835 A | * | 12/1988 | Elias ....................... | A61F 5/453 604/351 |
| 5,065,459 A | * | 11/1991 | Tjahaja ..................... | A61F 5/44 4/144.2 |
| 8,250,677 B2 | * | 8/2012 | Nicolosi ................ | A41B 9/023 2/403 |
| 8,961,482 B2 | | 2/2015 | Heyman | |
| 10,588,793 B2 | * | 3/2020 | Lumaque-Steeman ..................... | A61F 13/5616 |

(Continued)

FOREIGN PATENT DOCUMENTS

| | | |
|---|---|---|
| GB | 2489983 | 10/2012 |
| WO | WO 02/38088 A1 | 5/2002 |
| WO | WO 2016/189170 A1 | 12/2016 |

*Primary Examiner* — Andrew J Mensh
(74) *Attorney, Agent, or Firm* — Kattina V. Barsik, Esq.

(57) ABSTRACT

Disclosed is a male urinary flow directing device for involuntary and hygiene protection during urination. The device includes a hollow tubular body, a perforation line and an absorbent moisture collecting liner. The hollow tubular body extends between first and second end portions thereof, and defines a diameter thereof, and an inner circumferential profile along the first end portion. The hollow tubular body includes a plurality of foldable lines across which the hollow tubular body is folded to be formed. The perforation line is formed along the first end portion and extends across one of a foldable line. The liner is coupled along the inner circumferential profile. The hollow tubular body is wearable, and to fit various sizes is tearable along the perforation line to expand or converge the diameter. The liner along the first end portion absorbs urination drops while the hollow tubular body is removed.

14 Claims, 4 Drawing Sheets

(56) References Cited

U.S. PATENT DOCUMENTS

2002/0104148 A1\* 8/2002 Silverman ............ A61F 13/471
2/48

\* cited by examiner

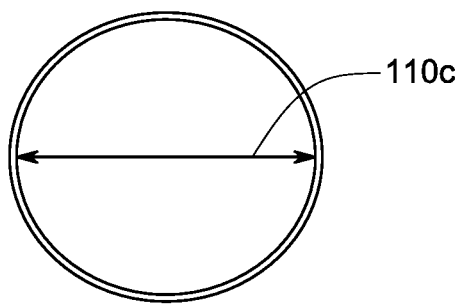
FIG. 2A
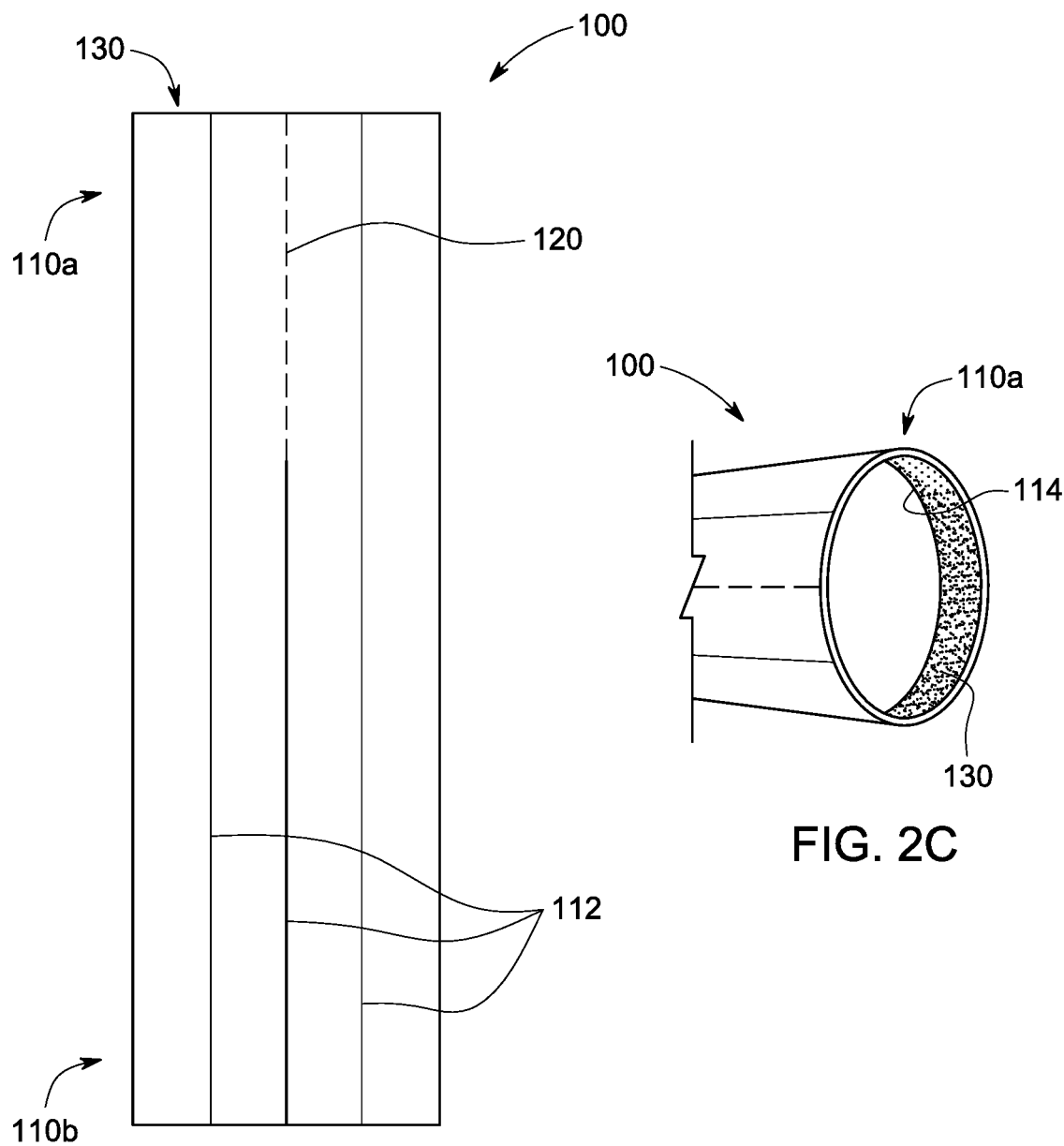
FIG. 2B
FIG. 2C

MALE URINARY FLOW DIRECTING DEVICE

CROSS REFERENCE TO RELATED APPLICATIONS

The present invention claims priority under 35 United States Code, Section 119 on the provisional application No. 62/751,372 filed on Oct. 26, 2018, the disclosure of which is incorporated by reference.

FIELD OF THE INVENTION

The present invention generally relates to involuntary and hygiene devices, and, more particularly, to a male urinary flow directing device for involuntary and hygiene protection during urination.

BACKGROUND OF THE INVENTION

Males, whether young or old, have always had a urine mist problem, because they are above the toilet when peeing. Then, there are other males who have never been taught to lift the toilet seat when urinating, instead they splash the seat. Most bathrooms that are used predominantly by males have a urine smell and must be washed regularly. Particularly late in life, there are unfortunately instances when a man's penis has too much flaccidity during urination to direct the flow of urine into the toilet or other urine receptacle. As a result, urine splashes or drips on the toilet seat or on the floor. As men advance in age their urinary aim and ability to aim their penis often decreases. There also are other men who have this challenge due to physical or other health related reasons. As a result, urine is unintentionally sprayed or dripped on the toilet seat or floors. This spray or drip then lingers outside the toilet and creates unhealthy conditions.

The lack of penis rigidity also may impact the cleanliness of the penis, resulting in urine spots on men's clothes.

Prior art shows more permanent means of maintaining more strength or rigidity in the penis to allow for better control of it. This permanent means addresses more severe cases of flaccidity and is generally more related to erectile disfunction rather than urinary issues.

Prior art also indicates contraptions for short or retracted penises or for utilization after prostate cancer. These items are generally much larger than this claim and lack the ease of portability and disposal as the present invention.

Prior art further reveals receptacles out of which the penis may slip out resulting in urine outside the receptacle.

Prior art also reveals items such as elevated toilets, toilets in a bag and adult diapers as ways to limit the overspray or leaking of urine during male urination. These proposals are alternative means of capturing urine and are of limited and impractical use in the public environment.

Accordingly, there exists a need to provide a convenient, discreet and disposable way to direct flow, as well as a way to capture the last drops of urine from the head of the penis. Men's restrooms often lack the toilet paper necessary to blot the excess drops of urine from the penis.

SUMMARY OF THE INVENTION

In view of the foregoing disadvantages inherent in the prior art, the general purpose of the present invention is to provide a male urinary flow directing device to include all advantages of the prior art, and to overcome the drawbacks inherent in the prior art.

In one aspect of the present invention, a male urinary flow directing device for involuntary and hygiene protection during urination is provided. The male urinary device includes a hollow tubular body, a perforation line, and an absorbent moisture collecting liner. The hollow tubular body extends between a first end portion, and a second end portion opposite to the first end portion. The hollow tubular body may define a diameter thereof and may include an inner circumferential profile along the first end portion. The hollow tubular body may have a plurality of foldable lines across which the hollow tubular body may be folded and formed. The perforation line may be formed along the first end portion and extends across at least one of a foldable line of the plurality of foldable lines. The absorbent moisture collecting liner may be coupled along the inner circumferential profile at the first end portion of the hollow tubular member. The hollow tubular body may be wearable from the first end portion thereof, and in order to fit various sizes may be tearable along the perforation line to expand or converge the diameter of the first end portion of the hollow tubular body. The absorbent moisture collecting liner along the first end portion may absorb urination drops while the hollow tubular body is removed.

In one embodiment, the male urinary flow directing device, or the hollow tubular body may be disposable and made from disposable materials.

In one embodiment, the hallow tubular body may include a predetermined length to accommodate various lengths.

In one embodiment, the perforation line may be formed up to a predetermined length across one of the foldable lines. The predetermined length of the perforation line may be smaller than a total length of the hollow tubular body extending between the first end portion and the second end portion.

In one embodiment, the absorbent moisture collecting liner may also be perforated along the perforation line.

In one embodiment, the diameter of the hollow tubular body along the first end portion and the second end portion are the same unless the perforation line is torn.

In one embodiment, the diameter of the hollow tubular body along the first end portion and the second end portion varies, either to expand or to converge when the perforation line is torn.

In one further aspect of the present disclosure, the method for making a male urinary flow directing device for involuntary and hygiene protection during urination is provided. The method includes: forming a hollow tubular body extending between a first end portion, and a second end portion opposite to the first end portion thereof. The hollow tubular body defines a diameter thereof, and an inner circumferential profile along the first end portion. The hollow tubular body may include a plurality of foldable lines across which the hollow tubular body is folded to be formed. Further, the method includes forming a perforation line along the first end portion to extend across at least one of a foldable line of the plurality of foldable lines. Furthermore, the method includes coupling an absorbent moisture collecting liner along the inner circumferential profile at the first end portion of the hollow tubular member. The hollow tubular body is wearable from the first end portion thereof, and to fit various sizes tearable along the perforation line to expand or converge the diameter of the first end portion of the hollow tubular body. Further, the absorbent moisture collecting liner along the first end portion absorbs urination drops while the hollow tubular body is removed.

In one embodiment, forming the perforation line includes forming the perforation line up to a predetermined length across one of the foldable lines.

In one embodiment, forming the perforation line also comprises perforating the absorbent moisture collecting liner along the perforation line.

In one further aspect of the present disclosure, a method for using a male urinary flow directing device for involuntary and hygiene protection during urination is provided. The method includes, inserting a hollow tubular body that is extending between a first end portion and a second end portion thereof. The hollow tubular body defines a diameter thereof. The hollow tubular body further defines an inner circumferential profile along the first end portion thereof. The hollow tubular body may include a plurality of foldable lines across which the hollow tubular body may be folded to be formed. The present method further includes tearing, if needed, the hollow tubular body along a perforation line, formed along the first end portion and extending across at least one of a foldable line of the plurality of foldable lines, to expand or converge the diameter of the first end portion of the hollow tubular body, to fit various sizes. The present method further includes absorbing urination drops while the hollow tubular body is being removed after urination.

This together with the other aspects of the present invention, along with the various features of novelty that characterize the present invention, is pointed out with particularity in the claims annexed hereto and forms a part of the present invention. For a better understanding of the present invention, its operating advantages, and the specified object attained by its uses, reference should be made to the accompanying drawings and descriptive matter in which there are illustrated exemplary embodiments of the present invention.

BRIEF DESCRIPTION OF THE DRAWINGS

The advantages and features of the present invention will become better understood with reference to the following detailed description and claims taken in conjunction with the accompanying drawings, wherein like elements are identified with like symbols, and in which:

FIG. 2A illustrates a front view of a male urinary flow directing device, in accordance with an embodiment of the present invention;

FIG. 2B illustrates a top view of a male urinary flow directing device, in accordance with an embodiment of the present invention;

FIG. 2C illustrates a perspective view of a male urinary flow directing device, in accordance with an embodiment of the present invention;

Like reference numerals refer to like parts throughout the description of several views of the drawings.

DETAILED DESCRIPTION OF THE INVENTION

Figure 1:
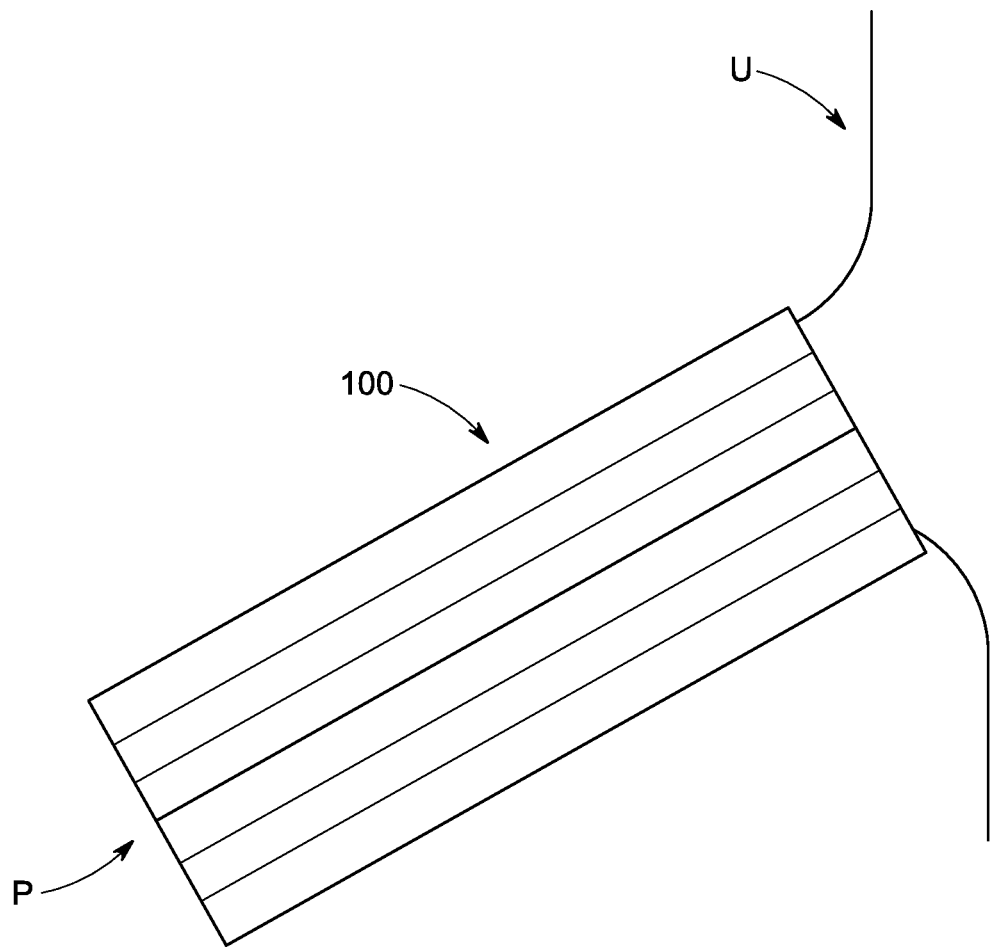
FIG. 1 illustrates a side view of a male urinary flow directing device worn by a user, in accordance with an embodiment of the present invention.

For a thorough understanding of the present invention, reference is to be made to the following detailed description, including the appended claims, in connection with the above-described drawings. Although the present invention is described in connection with exemplary embodiments, the present invention is not intended to be limited to the specific forms set forth herein. It is understood that various omissions and substitutions of equivalents are contemplated as circumstances may suggest or render expedient, but these are intended to cover the application or implementation without departing from the spirit or scope of the claims of the present invention. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The terms, "a" and "an" herein do not denote a limitation of quantity, but rather denote the presence of at least one of the referenced items.

The present invention has a means of providing penile support while directing urine flow. The present invention has a perforated feature accommodates different size penises. The present invention has an absorbent moisture collector which eliminates the last drops of urine that often spot clothing or drips onto the toilet seat or floor. The invention increases the hygiene around the toilet area and on clothes. While useful for boys and men of any age, because of its disposable nature the invention provides a discreet means for men to remain standing as they advance in age or if they have other challenges. The invention is light weight and folds small enough to fit in a suit, jacket or pants pocket. It can then be thrown away after use. The invention can be used in households and in medical offices, senior living facilities, hospitals and other facilities. The invention provides an alternative for improving hygiene at and away from home.

More specifically, the present invention provides a male urinary flow directing device for involuntary and hygiene protection during urination. The male urinary device includes a hollow tubular body, a perforation line, and an absorbent moisture collecting liner. The hollow tubular body extends between a first end portion, and a second end portion opposite to the first end portion. The hollow tubular body may define a diameter thereof and may include an inner circumferential profile along the first end portion. The hollow tubular body may have a plurality of foldable lines across which the hollow tubular body may be folded and formed. The perforation line may be formed along the first end portion and extends across at least one of a foldable line of the plurality of foldable lines. The absorbent moisture collecting liner may be coupled along the inner circumferential profile at the first end portion of the hollow tubular member. The hollow tubular body may be wearable from the first end portion thereof, and to fit various sizes may be tearable along the perforation line to expand or converge the diameter of the first end portion of the hollow tubular body.

The absorbent moisture collecting liner along the first end portion may absorb urination drops while the hollow tubular body is removed.

Referring now to FIG. 1, a side view of a male urinary flow directing device 100 hereinafter will be referred to as 'device 100' worn by a user 'U' around his penis 'P', in accordance with an embodiment of the present invention, is illustrated. The device 100 provides penile support to the user while directing urine flow into a receptacle, such as toilet, etc. The device 100 can accommodate different size penises and eliminates the last drops of wine that often spot clothing or drips onto the toilet seat or floor. The device 100 increases the hygiene around the toilet area and on clothes. While useful for boys and men of any age, because of its disposable nature the device 100 provides a discreet means for men to remain standing as they advance in age or if they have other challenges. The device 100 is light weight and folds small enough to fit in a suit, jacket or pants pocket. The device 100 can be thrown away after use. The device 100 can be used in households and in medical offices, senior living facilities, hospitals and other facilities. The device 100 also provides an alternative for improving hygiene at and away from home.

Figure 3A:
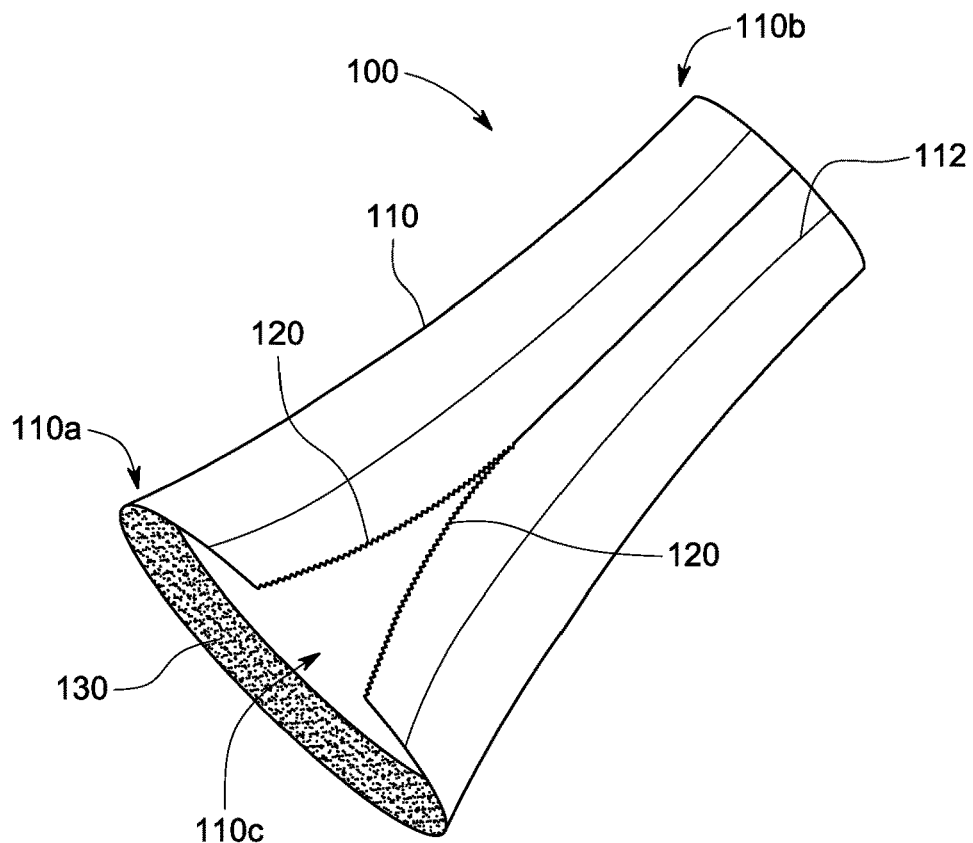
FIG. 3A illustrates a perspective view of a male urinary flow directing device torn along a perforation line to obtain an expanded state, in accordance with an embodiment of the present invention.
Figure 3B:
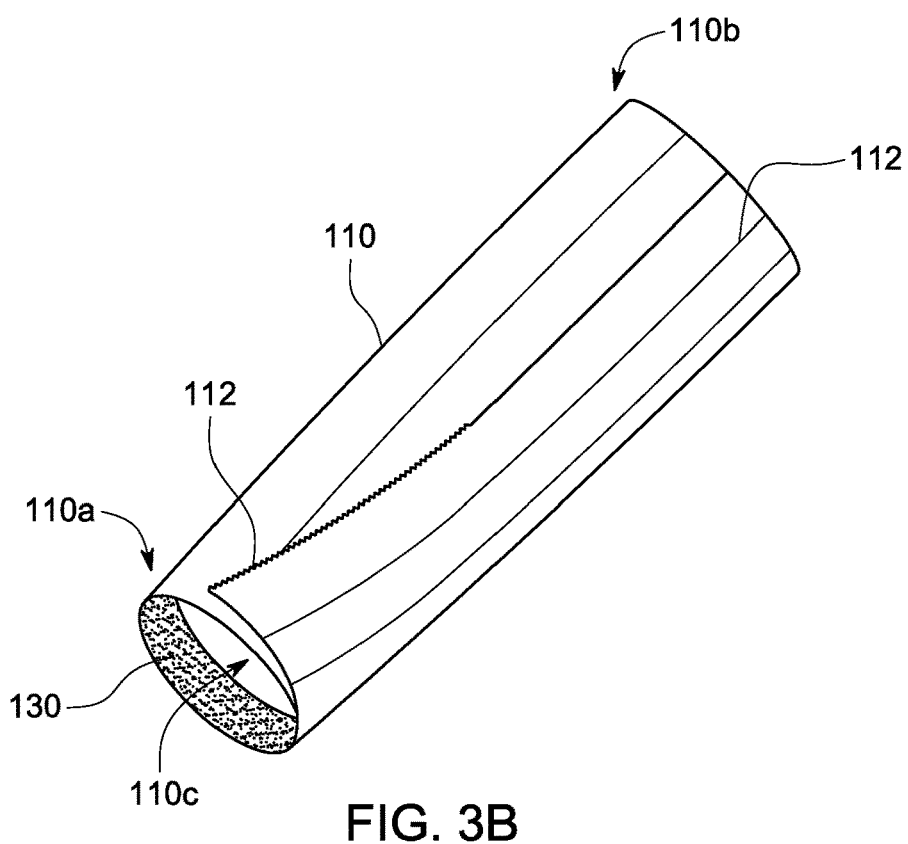
FIG. 3B illustrates a perspective view of a male urinary flow directing device torn along a perforation line to obtain a converged state, in accordance with an embodiment of the present invention.

The device 100 will now be explained in detail with reference to FIG. 2A to 3B, and in conjunction with FIG. 1. As shown, FIG. 2A illustrates a front view of the device 100; FIG. 2B illustrates a top view of the device 100; FIG. 2C illustrates a perspective view of the device 100, in accordance with an embodiment of the present invention. Further, FIG. 3A illustrates a perspective view of the device 100 torn to obtain an expanded state, in accordance with an embodiment of the present invention. Furthermore, FIG. 3B illustrates a perspective view of the device 100 in a converged state, in accordance with an embodiment of the present invention.

As shown in FIGS. 2A to 2C, the device 100 may include a hollow tubular body 110, a perforation line 120, an absorbent moisture collecting liner 130.

The hollow tubular body 110 may be configured to extend between a first end portion 110a and a second end portion 110b, opposite to the first end portion 110a thereof. The hollow tubular body 110 may define a diameter 110c, and an inner circumferential profile 114 along the first end portion 110a. Further, the hollow tubular body 110 may include a plurality of foldable lines 112 across which the hollow tubular body 110 may be folded and formed.

Further, the perforation line 120 may be formed along the first end portion 110a and extends across at least one of a foldable line 112a of the plurality of foldable lines 112. The perforation line 120 may be formed up to a predetermined length across one of the foldable lines 112. The predetermined length of the perforation line 120 may be smaller than a total length of the hollow tubular body 110 extending between the first end portion 110a and the second end portion 110b. In various embodiments, the diameter 110c of the hollow tubular body 110 along the first end portion 110a and the second end portion 110b may be the same unless the perforation line 120 is torn.

Further, the absorbent moisture collecting liner 130 may be coupled along the inner circumferential profile 114 at the first end portion 110a of the hollow tubular member 110. The absorbent moisture collecting liner 130 may also be perforated along the perforation line 120.

As shown in FIG. 1, The device 100 may be wearable. Specifically, the device 100 from the hollow tubular body 110 may be wearable from the first end portion 110a thereof. In one embodiment, the device 100 may completely accommodate the penis 'P' within the hollow tubular body 110, such that the penis 'P' must not extend beyond the hollow tubular body 110, as shown in FIG. 1. The diameter 110c of the hollow tubular body 110 along the first end portion 110a and the second end portion 110b varies, either to expand or to converge when the perforation line 120 is torn. Specifically, to fit various sizes of penis, the device 100 may be tearable along the perforation line 120 to expand or converge the diameter 110c of the first end portion 110a of the hollow tubular body 110. As specifically shown in FIG. 3A, the device 100 is torn along the perforation line 120 to obtain such expanded state. Further, FIG. 3B illustrates the device 100 torn along the perforation line 120 to obtain a converged state. Further, the absorbent moisture collecting liner 130 along the first end portion 110a absorbs urination drops while the hollow tubular body 110 is taken out from the penis 'P' of the user 'U' for disposal.

Figure 4:
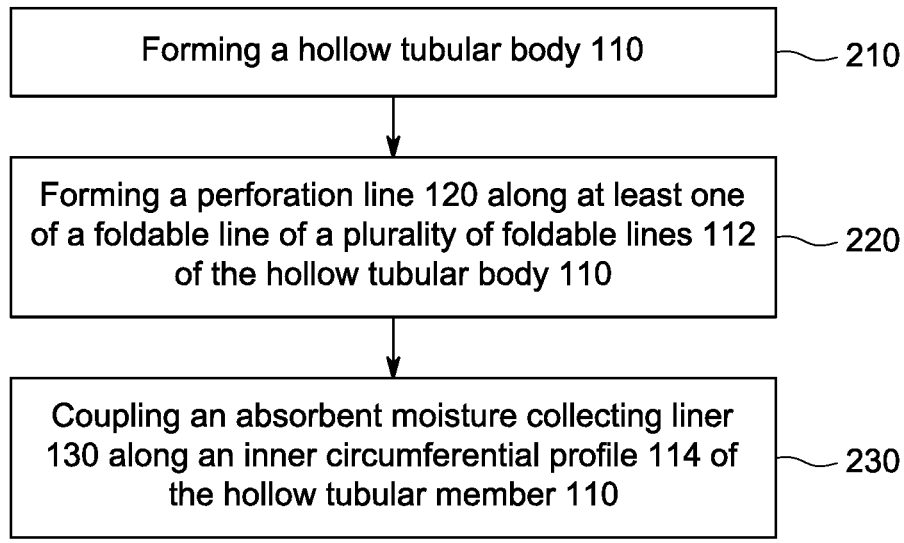
FIG. 4 illustrates a method for making a male urinary flow directing device, in accordance with an embodiment of the present invention.

Referring now to FIG. 4, a method for making a male urinary flow directing device, such as device 100, is provided. The method, at 200, forms a hollow tubular body 110, as described with reference to FIGS. 2A to 2C. Further, the method, at 210 forms a perforation line, such as the perforation line 120. Furthermore, at 220 the method includes coupling an absorbent moisture collecting liner, such as liner 130, along the inner circumferential profile 114 at the first end portion of the hollow tubular member 110. For the sake of brevity of this specification, detailed components of the device 100 is not explained herein to avoid repetition.

In one embodiment, forming the perforation line, at 210, may include forming the perforation line up to a predetermined length across one of the foldable lines.

In one further embodiment, forming the perforation line, at 210, also comprises perforating the absorbent moisture collecting liner along the perforation line.

Figure 5:
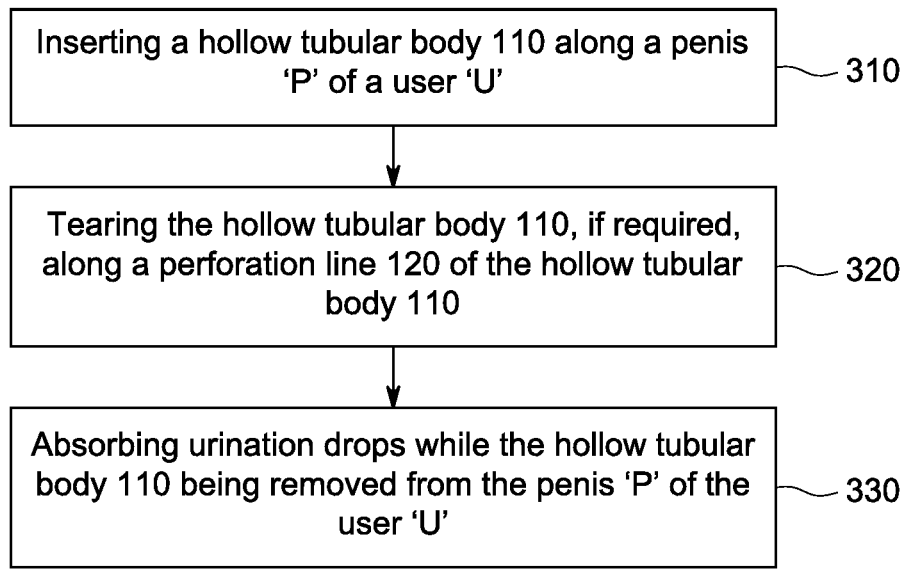
FIG. 5 illustrates a method for using a male urinary flow directing device, in accordance with an embodiment of the present invention.

Referring now to FIG. 5, a method for using a male urinary flow directing device, such as the device 100 is provided. The method, at 310, includes, inserting a hollow tubular body, such as the hollow tubular body 110, along the penis 'P' of the user 'U'. The method, at 320, includes tearing, if needed, the hollow tubular body along a perforation line, such as the perforation line 120, to expand or converge the diameter 110c of the first end portion 110a of the hollow tubular body 110, to fit various sizes. The method further includes, at 330, absorbing urination drops while the hollow tubular body is being removed from the penis 'P' of the user 'U' by a absorbent moisture collecting liner, such as the absorbent moisture collecting liner 130, after urination.

The present invention offers the various advantages. The present invention can accommodate different size penises and eliminates the last drops of urine that often spot clothing or drips onto the toilet seat or floor. The invention increases the hygiene around the toilet area and on clothes. The disposable nature of the invention provides a discreet means for men to remain standing as they advance in age or if they have other challenges. The invention is light weight and folds small enough to fit in a suit, jacket or pants pocket. It can then be thrown away after use. The invention can be used in households and in medical offices, senior living facilities, hospitals and other facilities. The invention provides an alternative for improving hygiene at and away from home.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, to thereby enable others skilled in the art to best utilize the present invention and various embodiments with various modifications as are suited to the particular use contemplated. It is understood that various omissions and substitutions of equivalents are contemplated as circumstance may suggest or render expedient, but such are intended to cover the application or implementation without departing from the spirit or scope of the claims of the present invention.

What is claimed is:

1. A male urinary flow directing device for involuntary and hygiene protection during urination, the male urinary device, comprising:
   a hollow tubular body extending between a first end portion, and a second end portion opposite to the first end portion thereof, the hollow tubular body defines a diameter thereof, and an inner circumferential profile along the first end portion, the hollow tubular body having a plurality of foldable lines across which the hollow tubular body is folded to be formed, each folded line of the plurality of foldable lines straightly extends across entire length, between the first end portion and the second end portion, of the hollow tubular body, and spaced-apart at equal distance from an adjacent folded line of the plurality of foldable lines;
   a perforation line formed along the first end portion and extends partially, up to a predetermined length, along at least one of a foldable line of the plurality of foldable lines;
   an absorbent moisture collecting liner coupled along the inner circumferential profile at the first end portion of the hollow tubular member,
   wherein the hollow tubular body is wearable from the first end portion thereof, and to fit various sizes is tearable along the perforation line to expand or converge the diameter of the first end portion of the hollow tubular body, while the diameter along the second end portion of the hollow tubular body is retained constant, and
   wherein absorbent moisture collecting liner along the first end portion absorb urination drops while the hollow tubular body is disposed.

2. The male urinary flow directing device of claim 1, wherein the hollow tubular body is disposable and made from disposable materials.

3. The male urinary flow directing device of claim 1, wherein the hollow tubular body comprises a predetermined length to accommodate various length.

4. The male urinary flow directing device of claim 1, wherein the predetermined length of the perforation line is smaller than a total length of the hollow tubular body extending between the first end portion and the second end portion.

5. The male urinary flow directing device of claim 1, wherein the absorbent moisture collecting liner is also perforated along the perforation line.

6. The male urinary flow directing device of claim 1, wherein the diameter the hollow tubular body along the first end portion and the second end portion are same unless the perforation line is torn.

7. The male urinary flow directing device of claim 1, wherein the diameter the hollow tubular body along the first end portion and the second end portion varies, either to expand or to converge when the perforation line is torn.

8. A male urinary flow directing device for involuntary and hygiene protection during urination, the male urinary device, comprising:
   a hollow tubular body extending between a first end portion, and a second end portion opposite to the first end portion thereof, the hollow tubular body defines a diameter thereof, and an inner circumferential profile along the first end portion, the hollow tubular body having a plurality of foldable lines across which the hollow tubular body is folded to be formed, each folded line of the plurality of foldable lines straightly extends across entire length, between the first end portion and the second end portion, of the hollow tubular body, and spaced-apart at equal distance from an adjacent folded line of the plurality of foldable lines;
   a perforation line formed along the first end portion and extends partially, up to a predetermined length, along at least one of a foldable line of the plurality of foldable lines, wherein the predetermined length of the perforation line is smaller than a total length of the hollow tubular body extending between the first end portion and the second end portion;
   an absorbent moisture collecting liner coupled along the inner circumferential profile at the first end portion of the hollow tubular member, wherein the absorbent moisture collecting liner is also perforated along the perforation line,
   wherein the hollow tubular body is wearable from the first end portion thereof, and to fit various sizes tearable along the perforation line to expand or converge the diameter of the first end portion of the hollow tubular body, while the diameter along the second end portion of the hollow tubular body is retained constant, and
   wherein absorbent moisture collecting liner along the first end portion absorb urination drops while the hollow tubular body is disposed.

9. The male urinary device of claim 8, wherein the diameter the hollow tubular body along the first end portion and the second end portion are same unless the perforation line is torn.

10. The male urinary device of claim 8, wherein the diameter the hollow tubular body along the first end portion and the second end portion varies, either to expand or to converge when the perforation line is torn.

11. A method for making a male urinary flow directing device for involuntary and hygiene protection during urination, the method comprising:
   forming a hollow tubular body extending between a first end portion, and a second end portion opposite to the first end portion thereof, the hollow tubular body defines a diameter thereof, and an inner circumferential profile along the first end portion, the hollow tubular body having a plurality of foldable lines across which the hollow tubular body is folded to be formed, each folded line of the plurality of foldable lines straightly extends across entire length, between the first end portion and the second end portion, of the hollow tubular body, and spaced-apart at equal distance from an adjacent folded line of the plurality of foldable lines;
   forming a perforation line along the first end portion to extend partially, up to a predetermined length, along at least one of a foldable line of the plurality of foldable lines; and
   coupling an absorbent moisture collecting liner along the inner circumferential profile at the first end portion of the hollow tubular member, wherein the hollow tubular body is wearable from the first end portion thereof, and to fit various sizes tearable along the perforation line to expand or converge the diameter of the first end portion of the hollow tubular body, while the diameter along the second end portion of the hollow tubular body is retained constant, and wherein absorbent moisture collecting liner along the first end portion absorb urination drops while the hollow tubular body is disposed.

12. The method of claim 11, wherein forming the perforation line comprises forming the perforation line up to thea predetermined length along one of the foldable lines.

13. The method of claim 11, wherein forming the perforation line also comprises perforating the absorbent moisture collecting liner along the perforation line.

14. A method for using a male urinary flow directing device for involuntary and hygiene protection during urination, the method comprising:

inserting a hollow tubular body along a penis of a user, the hollow tubular body extending between a first end portion, and a second end portion, opposite to the first end portion thereof, the hollow tubular body defines a diameter thereof, and an inner circumferential profile along the first end portion, the hollow tubular body having a plurality of foldable lines across which the hollow tubular body is folded to be formed, each folded line of the plurality of foldable lines straightly extends across entire length, between the first end portion and the second end portion, of the hollow tubular body, and spaced-apart at equal distance from an adjacent folded line of the plurality of foldable lines;

tearing, if needed, the hollow tubular body along a perforation line, formed along the first end portion and extends partially, up to a predetermined length, along at least one of a foldable line of the plurality of foldable lines, to expand or converge the diameter of the first end portion of the hollow tubular body, to fit various sizes, while the diameter along the second end portion of the hollow tubular body is retained constant; and absorbing urination drops while the hollow tubular body being removed after urination.

* * * * *